United States Patent [19]

Wang et al.

[11] Patent Number: 4,907,590
[45] Date of Patent: Mar. 13, 1990

[54] ACUPUNCTURE THERAPY BY BURYING SUTURE THROUGH AN ACUPUNCTURE NEEDLE

[76] Inventors: Li-Li Wang; Hsieuh-Li Chin, both of No. 10, Lane 101, Chieng-Kuo First Rd., Kaohsiung City, Taiwan

[21] Appl. No.: 224,006

[22] Filed: Jul. 25, 1988

[51] Int. Cl.⁴ .............................................. A61B 17/34
[52] U.S. Cl. ..................... 606/139; 606/189; 606/222
[58] Field of Search ................. 128/340, 339, 329 A, 128/330

[56] References Cited

U.S. PATENT DOCUMENTS

| | | | |
|---|---|---|---|
| 1,059,631 | 4/1913 | Popovics | 128/330 |
| 3,013,559 | 12/1961 | Thomas | 128/340 |
| 3,943,932 | 3/1976 | Woo | 128/329 A |
| 3,976,078 | 8/1978 | Toriello | 128/329 A |
| 4,160,453 | 6/1979 | Miller | 128/330 |
| 4,161,943 | 6/1979 | Nogier | 128/329 A |
| 4,479,496 | 10/1984 | Hso | 128/329 A |
| 4,790,830 | 12/1988 | Hamacher | 604/274 |

OTHER PUBLICATIONS

*Harrison's Principles of Internal Medicine,* Gpetersdorf et. al., 1983, 1162–1167.
Lee, Jane; Cheung, C.; *Current Acupuncture Therapy,* 1978, pp. 93–95, 230–234.

*Primary Examiner*—C. Fred Rosenbaum
*Assistant Examiner*—Mark O. Polutta

[57] ABSTRACT

An acupuncture therapy is performed by using a disposable acupuncture needle comprising a suture which is preferably made of absorbable material, a handle having a suture holder in which one end of the suture is held integrally, a barrel which the handle is insertable into an engageable with, a hollow needle which is integrated with the barrel and through which the suture is insertable, a tube through which the barrel together with the needle is slidable and a cap which is engageable with one end of the tube to cover the needle so as to prevent contamination. The suture is so disposed that it has a small portion going out of the needle tip so that when the needle is pulled out of the human body, the suture is left in the human body to provide long term therapy until the suture is absorbed by the human body.

2 Claims, 5 Drawing Sheets

ACUPUNCTURE THERAPY BY BURYING SUTURE THROUGH AN ACUPUNCTURE NEEDLE

BACKGROUND OF THE PRESENT INVENTION

This invention relates to a disposable acupuncture needle.

Acupuncture is a branch of the traditional Chinese medicine. The basic idea of acupuncture is to puncture or moxa-cauterize the human body at certain points which are called vital points to stimulate and initiate the human body's physiological potential so as to recover human physiological function and cure disease. Conventional acupuncture, however, has drawbacks and inconvenience in treating the patients suffering chronic diseases or diseases giving uncontrollable pain. Usually, a patient with such diseases needs to be treated several times every two or three days in order to restore health. This is inconvenient for the patients.

Recently, in order to obviate the above drawbacks, new therapeutics have been developed. The new therapeutics combine the advantages of the traditional acupuncture and modern medicine. One of the new therapeutics is to incise skin and muscle in the vital point and then implant a catgut in the muscle. Another one of such therapeutics is also an incision of human body. But, instead of simply implanting a section of catgut in the human body, there are one or several buried sutures around the muscle and/or ligament in the vital point. Since both therapeutics need surgical operation, the patient inevitably has to suffer the uncomfortableness of the operation.

It is therefore the object of the present invention to disclose an acupuncture therapy by using a disposable acupuncture needle which can provide the same therapy as the above-mentioned modern therapeutics but without any surgical incision and risk of infection.

SUMMARY OF THE INVENTION

It is the primary object of the present invention to disclose an acupuncture therapy by using an acupuncture needle which is able to impmlant a section of suture in the human body without surgical operation.

It is another object of the present invention to provide an acupuncture needle which is disposable so that no sterilization of the used acupuncture needles is necessary.

Other objects and advantages of this invention will be obtained by those having ordinary skill in the art when the following detailed description has been read in conjunction with the accompanying drawings, in which:

DETAILED DESCRIPTION OF THE PREFERRED EMBODIMENT

Figure 1:
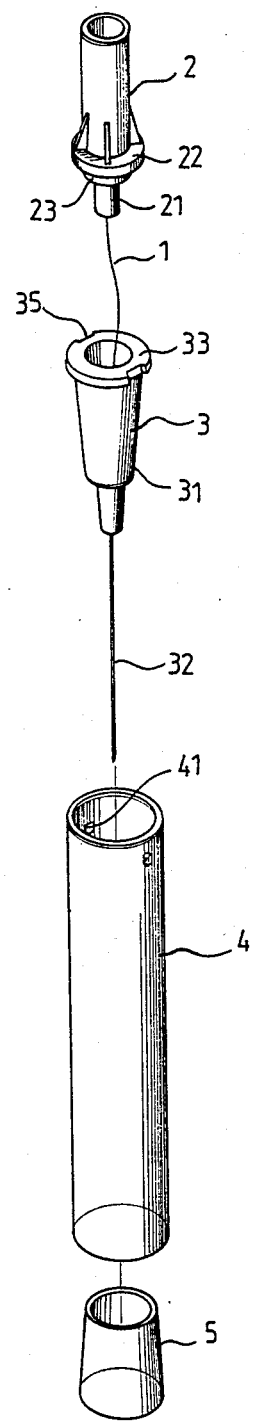
FIG. 1 is a perspective view of an embodiment in accordance with the present invention.

For purpose of promoting an understanding of the principles of the invention, reference will be made to the embodiment illustrated in the drawings. It will, nevertheless, be understood that no limitation of the scope of the invention is thereby intended, such alternatives and further modifications in the illustrated device and such further applications of the principles of the invention as illustrated herein being contemplated as would normally occur to one skilled in the art to which the invention relates.

Figure 2:
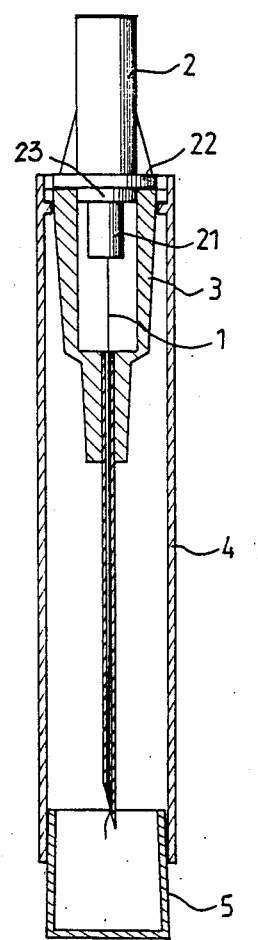
FIG. 2 is a cross-sectional view of the embodiment shown in FIG. 1.
Figure 3:
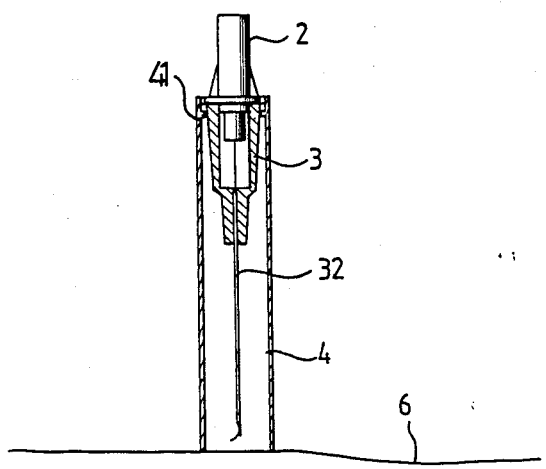
FIGS. 3, 4, 5 and 6 show the procedure of applying the embodiment shown in FIGS. 1 and 2 to the human body.

With reference to FIG. 1 and 2, an acupuncture needle of the present invention consists of a suture 1, a handle 2, a needle barrel 3, a tube 4 and a needle cap 5. The suture 1 is preferably an absorbable surgical suture, such as catgut or other FDA approved material (for example, Dexon suture), which will be absorbed by the human body after implanted in the human body. The suture 1 is held integrally by a suture holder 21 integrated with the handle 2. The handle 2 has a circumferential flange 22 which is disposed between the handle 2 and the suture holder 21. Further disposed between the flange 22 and the holder 21 is an engaging disc 23 of which the diameter is greater than that of the holder 21 and less than that of the flange 22. The needle barrel 3 which is preferably made of transparent or translucent plastic material is majorly constituted by a barrel 3 of which the inside dimension is the same as or slightly less than the outside diameter of the engaging disc 23 so that the suture holder 21 and the engaging disc 23 is insertable into and engageable with the barrel 31. Since the outside diameter of the flange 22 is greater than the diameter of the barrel 3, the insertion will be stopped when they contact each other. A hollow needle 32 is disposed under and integrated with the barrel 31. The suture 1 is insertable through the barrel 31 and the hollow needle 32. The length of the suture is such that when the handle 2 engages with the barrel 3, the suture 1 is slightly longer than the needle 32 and thus a portion of the suture goes out of the needle. Disposed on the barrel is a circular flange 33 with two notches 35. The diameter of the circular flange 33 is greater than that of the barrel 3.

The tube is also preferably made of transparent or translucent plastic material. The inside diameter of the tube is substantially the same as the outside diameter of the circular flange 33 of the barrel 3. Disposed inside and proximately to one end of the tube are two projections, corresponding to the notches 35, so that when the notches 35 match the projections 41, the barrel 3 is slidable through the tube 4. On the other end of the tube, the cap 5 which is preferably made of elastic material is elastically engageable with the tube 4 so as to cover one end of the tube 4 and prevent the needle 32 and the suture 1 from being contaminated.

Figure 4:
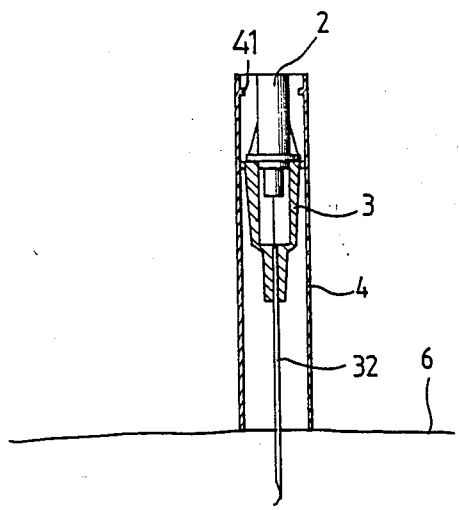
Figure 5:
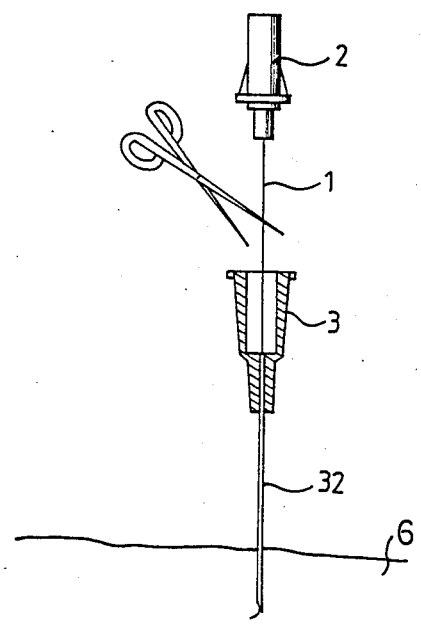
Figure 6:
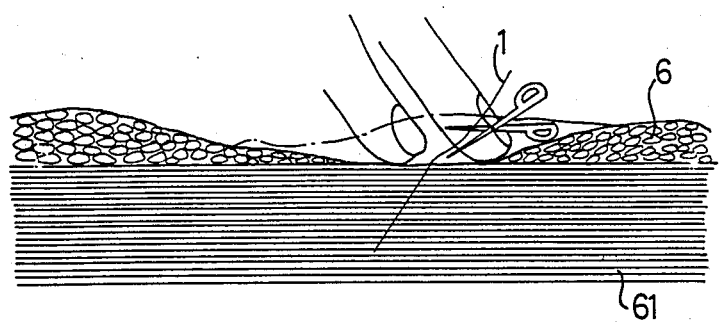
Figure 7:
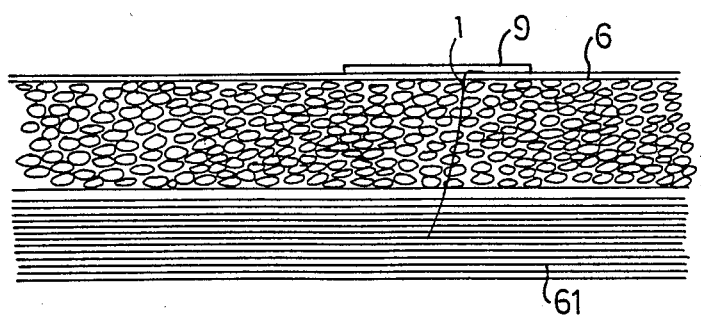
FIG. 7 shows another application with the present invention wherein the suture exposed to air is not cut off.

In order to show how to apply the acupuncture needle in accordance with the present invention, reference is now made to FIGS. 3, 4, 5 and 6. To use the acupuncture needle, the vital points in which the acupuncture is applied are located first. Then, the cap 5 is removed and the handle 2 is so rotated that the notches 35 match the projection 41. The needle 32 is pushed down to puncture the human body and further pushed to the desired depth, as shown in FIG. 4. The tube 4 is removed. The handle 2 is then separated from the barrel 31 and a section of the suture 1 is exposed between the handle 2 and the barrel 31. This section of suture is cut off and the handle 2 is removed, as shown in FIG. 5. Next, the needle barrel 3 is removed from the human body 6. Since a small portion of the suture 1 has gone out of the needle tip, the frictional force between the muscle 61 and the suture 1 will keep the suture 1 in the human body while the needle 32 is removed. Usually only the portion of the suture which reaches the muscle 61 is necessary for treatment, an outermost tip protruding outwardly beyond a skin of the human body should be removed in order to keep the suture 1 from being touched. To remove the outermost tip of the suture, the human body around the vital point is so depressed that the extra portion of the suture is exposed and then cut off, as shown in FIG. 6. After that, the suture will be completely implanted in the muscle to provide long term therapy.

If, under certain conditions, (for instance, the patient is allergic to the suture) it is necessary to withdraw the suture from the patient's body, the outermost tip of the suture, therefore, should be left and covered with adhesive tape 9. The tape 9 has preferably no adhesive in the central portion under which the suture 1 is covered. This is to prevent the suture from being pulled out unintentionally.

Although this invention has been described with a certain degree of particularity, it is understood that the present disclosure is made by way of example only and that numerous changes in the detail of construction and the combination and arrangement of parts may be resorted to without departing from the spirit and scope of the invention as hereinafter claimed.

I claim:

1. An acupuncture therapy comprising implanting a suture into a human body by using an acupuncture needle comprising a handle which is integrated with a suture holder and which is insertable into and engageable with the barrel portion of a needle barrel, a suture which is held integrally by said suture holder, a needle barrel which is constituted by a barrel integrated with a flange having a plurality of notches disposed thereon and a hollow needle disposed thereunder and through which said suture is insertable, a tube which has a plurality of projections, corresponding to said notches, disposed therein and which is engageable with said barrel and a cap which is engageable with one end of said tube to cover the needle and to prevent the needle from being contaminated, said barrel being slidable further into and through said tube when said projections match said notches, said suture which is inserted in the needle barrel having a small portion protruding outwardly from a tip of said needle;

the improvement which comprises:
said acupuncture therapy including the following steps:
A. Moving the acupuncture needle towards a location or area to be acupunctured and removing the cap from the tube;
B. Rotating the notches in said needle barrel to match said projections in said tube;
C. Depressing said handle to lower said needle puncture the human body to a desired depth and then removing said tube;
D. Separating said handle from said needle barrel to expose a section of said suture between said handle and said needle barrel;
E. Cutting said section of said suture between said handle and said needle barrel and removing said handle;
F. Withdrawing said needle from the human body to leave a small portion of said suture protruding beyond said tip of said needle to poke into a muscle in the human body for acupuncture treatment.

2. An acupuncture therapy comprising implanting a suture into a human body by using an acupuncture needle comprising a handle which is integrated with a suture holder and which is insertable into and engageable with the barrel portion of a needle barrel, a suture which is held integrally by said suture holder, a needle barrel which is constituted by a barrel integrated with a flange having a plurality of notches disposed thereon and a hollow needle disposed thereunder and through which said suture is insertable, a tube which as a plurality of projections, corresponding to said notches, disposed therein and which is engageable with said barrel and a cap which is engageable with one end of said tube to cover the needle and to prevent the needle from being contaminated, said barrel being slidable further into and through said tube when said projections match said notches, said suture which is inserted in the needle barrel having a small portion protruding outwardly from a tip of said needle;

the improvement which comprises:
said acupuncture therapy including the following steps:
A. Moving the acupuncture needle towards a location or area to be acupunctured and removing the cap from the tube;
B. Rotating the notches in said needle barrel to match said projections in said tube;
C. Depressing said handle to lower said needle to puncture the human body to a desired depth and then removing said tube;
D. Separating said handle from said needle barrel to expose a section of said suture between said handle and said needle barrel;
E. Cutting said section of said suture between said handle and said needle barrel and removing said handle;
F. Withdrawing said needle from the human body to leave a small portion of said suture protruding beyond said tip of said needle to poke into a muscle in the human body for acupuncture treatment;
G. Depressing the skin of the human body around the acupuncture area to reveal an outermost tip of the suture implanted in the human body, and cutting said outermost tip of said suture to leave said section of said suture in the human body for acupuncture treatment; and
H. Covering the outermost tip of said suture protruding outwardly from the skin of the human body by a tape.

* * * * *